United States Patent [19]
Menke

[11] 4,168,460
[45] Sep. 18, 1979

[54] PARTICLE SORTING APPARATUS

[75] Inventor: Everhard Menke, Munich, Fed. Rep. of Germany

[73] Assignee: Max-Planck Gesellschaft zur Förderung der Wissenschaften e.V., Göttingen, Fed. Rep. of Germany

[21] Appl. No.: 817,888

[22] Filed: Jul. 21, 1977

[30] Foreign Application Priority Data

Jul. 22, 1976 [DE] Fed. Rep. of Germany ....... 2632962

[51] Int. Cl.$^2$ ............................................. G01N 27/00
[52] U.S. Cl. .................................. 324/71 CP; 324/64
[58] Field of Search ...................... 209/3, 74 R, 127 R; 324/71 CP; 346/75; 356/39, 73, 104; 424/3

[56] References Cited

U.S. PATENT DOCUMENTS

| | | | |
|---|---|---|---|
| 3,380,584 | 4/1968 | Fulwyler | 324/71 CP |
| 3,710,933 | 1/1973 | Fulwyler et al. | 209/3 |
| 3,793,587 | 2/1974 | Thom et al. | 324/71 CP |
| 3,944,917 | 3/1976 | Walter et al. | 324/71 CP |
| 3,982,182 | 9/1976 | Hogg | 324/71 CP |

Primary Examiner—M. Tokar
Attorney, Agent, or Firm—Edwin E. Greigg

[57] ABSTRACT

A particle sorting and analyzing apparatus operating on the Coulter principle, with two chambers containing an electrolyte which is caused to flow through an orifice connecting the two chambers. The particles to be analyzed are introduced into the first chamber just ahead of the orifice. An electric field is established in the electrolyte by two electrodes, located in the first and second chamber, respectively. After passing out of the second chamber through an atomizing nozzle, selected droplets containing particles are charged and then deflected. The electrical currents generated by the charging processes are kept from interacting with the measuring currents by a third electrode, located in the second chamber in the vicinity of the nozzle and kept at the same potential as the other electrode in the second chamber. The third electrode effectively short-circuits the current path in the second chamber and grounds out spurious electrical disturbances.

7 Claims, 5 Drawing Figures

PARTICLE SORTING APPARATUS

BACKGROUND OF THE INVENTION

The invention relates to an apparatus for separating and sorting particles flowing in a suspension through chambers having multiple detection means. These detection means may be electrodes which receive current pulses produced when particles pass a measuring orifice and correspond to preset criteria.

More particularly, the invention relates to an apparatus of the above described type in which liquid drops containing the selected particles are provided with a static charge and are subsequently deviated in an appropriate way to enter collection stations for analysis. The deviation may be by electrical and/or magnetic means.

Particle sorters and separators of this type, in which particles are identified and separated according to the Coulter Principle are known and are described for example in U.S. Pat. No. 3,380,584, U.S. Pat. No. 3,710,933 and in various articles in the professional literature, for example Steinkamp, et. al., "A New Multiparameter Separator for Microscopic Particles and Biological Cells," Rev. Sci. Instrum., Vol. 44, No. 9, September 1973, p. 1301–1310; Fulwyler, "Electronic Separation of Biological Cells by Volume", Science, Vol. 150, Nov. 11, 1965, p. 910–911.

It is a basic fault of the known particle separators that the measuring current circuit between the two main electrodes picks up spurious and disturbing pulses from various sources. In spite of sometimes very expensive shielding it has heretofore been impossible to completely eliminate these spurious disturbances. An attempt to overcome this problem is described for example in U.S. Pat. No. 3,710,933, column 7, lines 60–63.

OBJECT AND SUMMARY OF THE INVENTION

It is thus a principal object of the invention to provide a particle separator of the type described above in which the measuirng circuit is not subject to spurious and disruptive pulses.

A detailed analysis of the causes of these disturbances has shown that they derive mainly from the charging pulses which the charging electrode generates for charging the particle stream and that these charging pulses are coupled into the main measuring circuit via the electrode contained in the second chamber of the apparatus.

The above stated object of the invention is thus achieved by providing an apparatus in which the second chamber of the separator is equipped with a secondary electrode which is maintained at the same electrical potential as the first or main electrode contained in the second chamber. Accordingly, the current path between the injection nozzle and the main electrode in the second chamber which constitutes the return electrode for the measuring current is virtually short circuited. Accordingly, the disturbances previously picked up by the measuring circuit are completely removed and measurements free from spurious results and disturbances are made possible.

The invention will be better understood as well as further objects and advantages thereof become more apparent from the ensuing detailed description of two exemplary embodiments taken in conjunction with the drawing.

BRIEF DESCRIPTION OF THE DRAWING

FIG. 1b is the equivalent circuit diagram for the particle separator shown in FIG. 1a;

FIG. 2b is the equivalent circuit for the apparatus illustrated in FIG. 2a;

DESCRIPTION OF THE PREFERRED EMBODIMENTS

Figure 1A:
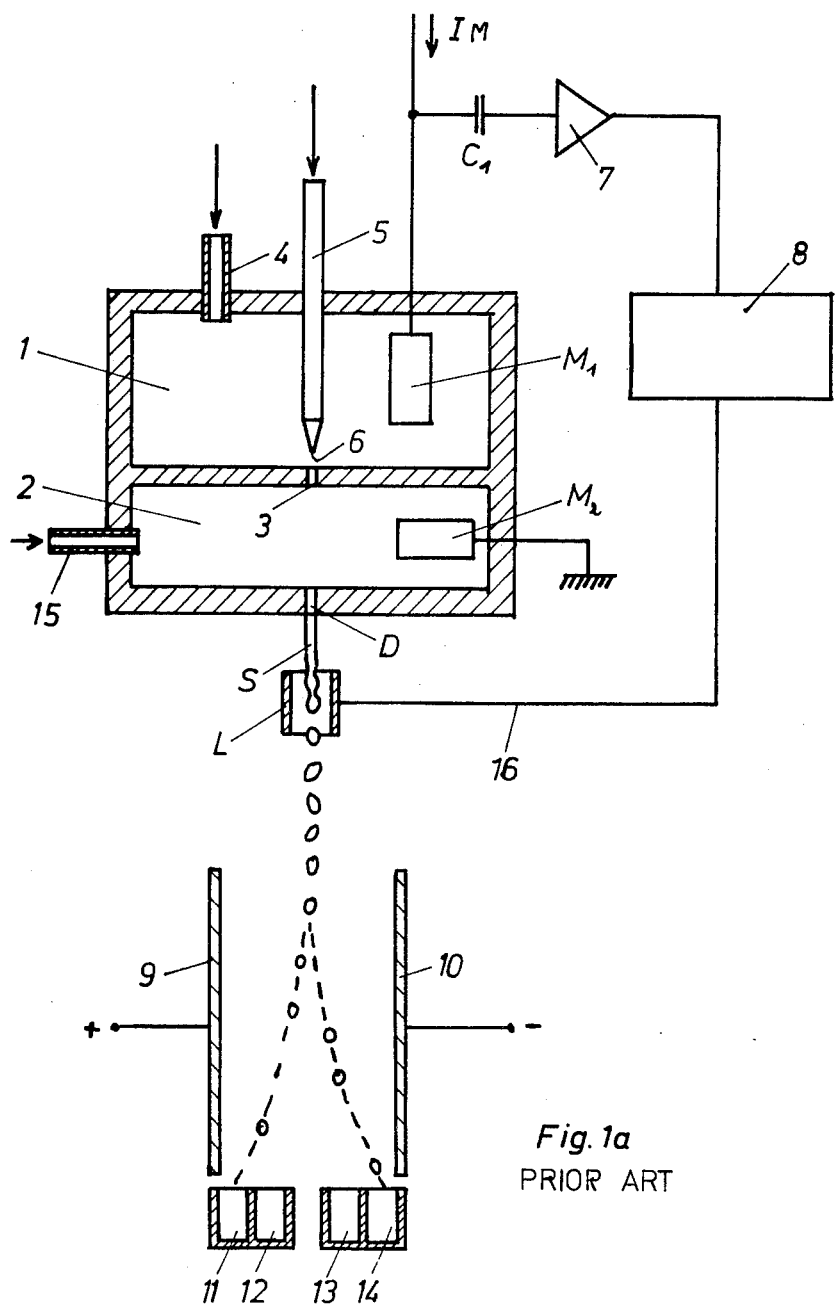
FIG. 1a is a schematic diagram of an apparatus for separating particles similar to those known in the art.
Figure 1:
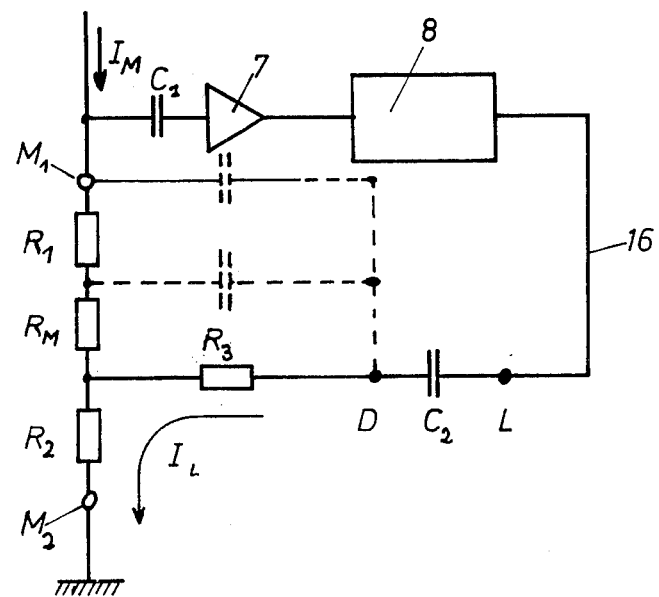

Turning now to FIG. 1a, which illustrates a known particle separator, there is found a first chamber 1 and a second chamber 2 which communicate through a measuring orifice 3. The first chamber 1 receives electrolyte through a conduit 4. Due to the reduced pressure in the second chamber 2, a flow of electrolyte is generated through the measuring aperture 3 from the first chamber 1 to the second chamber 2. Extending into the first chamber 1 is a supply capillary tube 5. The terminus 6 of the capillary tube 5 is located just ahead of the measuring aperture 3. The supply capillary tube 5 serves to admit particles, the volume and characteristics of which are to be analyzed and which are held in a liquid suspension. This suspension is introduced into the electrolyte stream just ahead of the measuring orifice 3. Located within the first chamber 1 is the first electrode $M_1$ and located in the second chamber 2 is a second electrode $M_2$. Under the influence of a source of potential not shown, a measuring current $I_m$ flows from the electrode $M_1$ through the electrolyte and through the measuring orifice 3 to the second electrode $M_2$. Whenever a particle passes the measuring orifice 3, it displaces the electric field lines therein and thus produces a temporary change $\Delta R_m$ of the electrical resistance $R_m$ which normally obtains between the two electrodes $M_1$ and $M_2$. As a result, there occurs across the resistance $R_M$ a voltage spike of magnitude $\Delta U_M = R_M \times I_M$ whose amplitude is proportional to the volume of the particle passing through the measuring orifice 3. The voltage pulse $\Delta U_M$ is transmitted via the coupling capacitor $C_1$ to an amplifier 7 and hence to a processor and control unit 8 in which the signal is analyzed. All of the elements so far described are known and pertain to the known Coulter apparatus described in U.S. Pat. No. 2,656,508.

The electronic processor and control unit 8 performs an analysis on the basis of predetermined criteria which permit a separation of the particles according to the signals which they produce. For example, when the output signal of the amplifier 7 falls above or below a predetermined value, the control unit 8 produces a charging pulse. This charging pulse serves to place an electrostatic charge on one or more droplets of the electrolyte which contain a selected particle. When the droplets then pass in between plates 9 and 10 across which a high electrostatic field is maintained, they experience a deviation which depends on the magnitude of their own charge. In this manner, the particles may be separated on the basis of the measurement of their volume and the corresponding charge and may be collected in various vessels 11, 12, 13, or 14. This separation is enhanced by spraying the electrolyte from the second chamber 2 through a nozzle D. In order to provide sufficient pressure for spraying the electrolyte from nozzle D and also to counteract a possibly high pressure drop across the measuring orifice 3, an additional amount of electrolyte fluid may be provided to the second chamber through a line 15. The spary nozzle D emits a stream of particles S which is formed as droplets shortly after leaving the nozzle. The formation of droplets, i.e. atomization, may be enhanced by an ultrasonic generator not shown. The stream of particles, i.e. the individual droplets, then enter a tubular charging electrode L. This electrode is connected to an output of the electronic processor and control unit 8 by a line 16. Whenever the processor unit 8 determines that a particle passing the orifice 3 has satisfied a given condition which is contained within the unit, it provides a delayed charging pulse to the charging electrode L. The delay corresponds to the normal time reqired by the particle to pass from the orifice 3 to the charging electrode L. The charging pulse U(t) given to the charging electrode L causes the droplet contained in the tube L to acquire a static charge which then causes its deviation during the passage through the electrostatic plates 9 and 10. The additional elements of the apparatus relating to the charging mechanism are also known, for example from the literature references above. The known apparatus, however, which will be discussed in detail with reference to FIG. 1b, has a distinct disadvantage of being subject to disturbing pulses in the measuring circuit between the electrodes $M_1$ and $M_2$, due to the charging pulses delivered to the charging electrode L. The eqivalent circuit of FIG. 1b shows a resistance $R_1$ which is the resistance between the electrode $M_1$ and the measuring orifice 3. The resistance $R_M$ is the resistance of the orifice 3; the resistance $R_2$ is the resistance between the orifice 3 and the electrode $M_2$ which is grounded. A resistance $R_3$ is shown as that part of the overall resistance between the nozzle D and the electrode $M_2$ which is not traversed by the measuring current $I_M$. The charging electrode L and the nozzle D are shown to be coupled through an effective capacitance $C_2$ which is equivalent to the capacitance of the charging electrode L with respect to the particle stream S which has a galvanic connection to the nozzle D.

It will be appreciated that when the charging electrode L receives a charging pulse U(t), a charging current of magnitude $I_L = C_2 \cdot dU(t)/dt$ passes through the resistances $R_3$ and $R_2$. This charging pulse is superimposed on the measuring current $I_M$ which flows between the two electrodes $M_1$ and $M_2$ and manifests itself as a spurious disturbance. In other words, disturbing pulses of magnitude $I_L R_2$ are superimposed on the measuring pulses $\Delta U_M$. Furthermore, the charging current-induced voltages formed across the resistors $R_2$ and $R_3$, i.e. voltages of magnitude $U_L = (R_2 + R_3) \cdot I_L$ are coupled capacitively into the first chamber 1 via spurious capacitances illustrated in FIG. 1b by dashed lines and thus lead to erroneous indications and/or falsifications of the actual measuring pulses. These various disturbances have made it impossible heretofore to make practical use of the known apparatus for the routine analysis of very large numbers of samples.

Figure 2A:
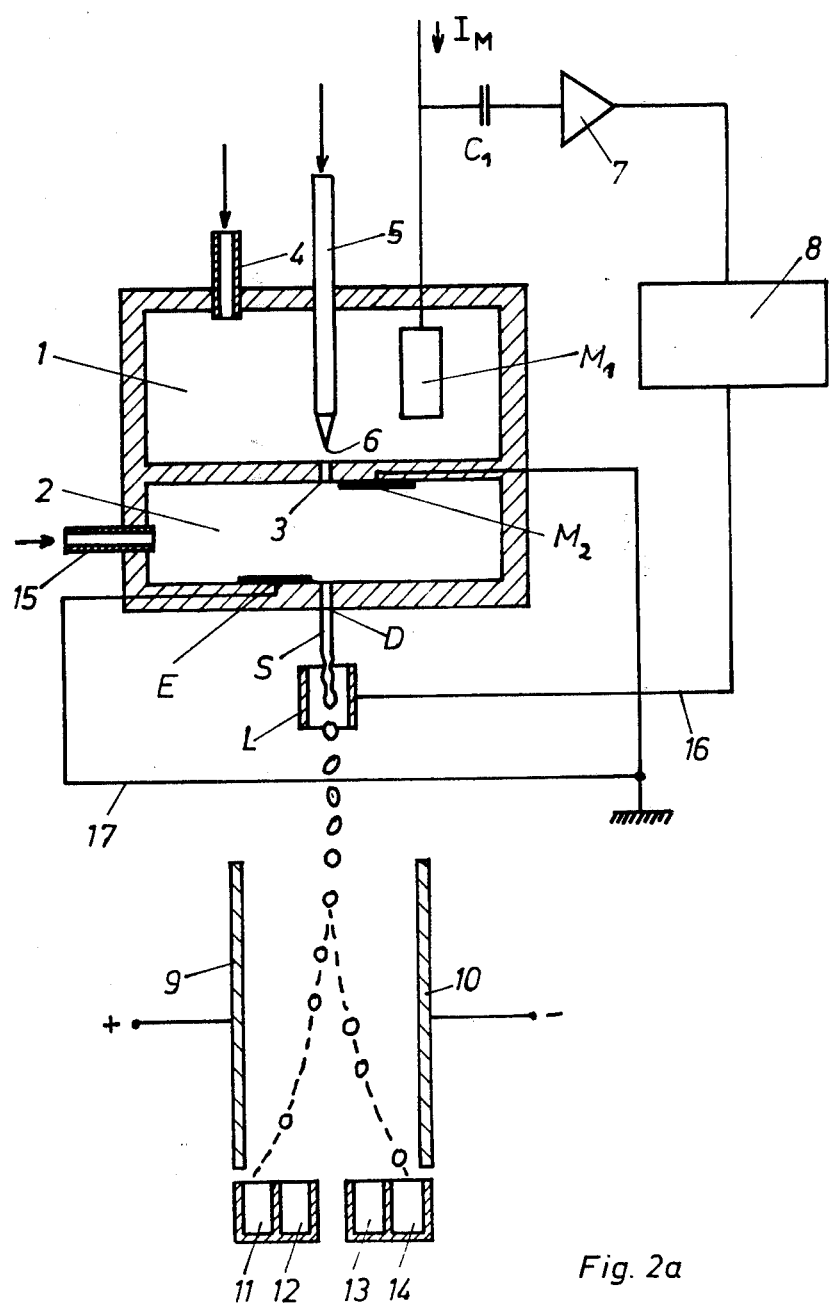
FIG. 2a is an illustration of a first exemplary embodiment of the invention.
Figure 2B:
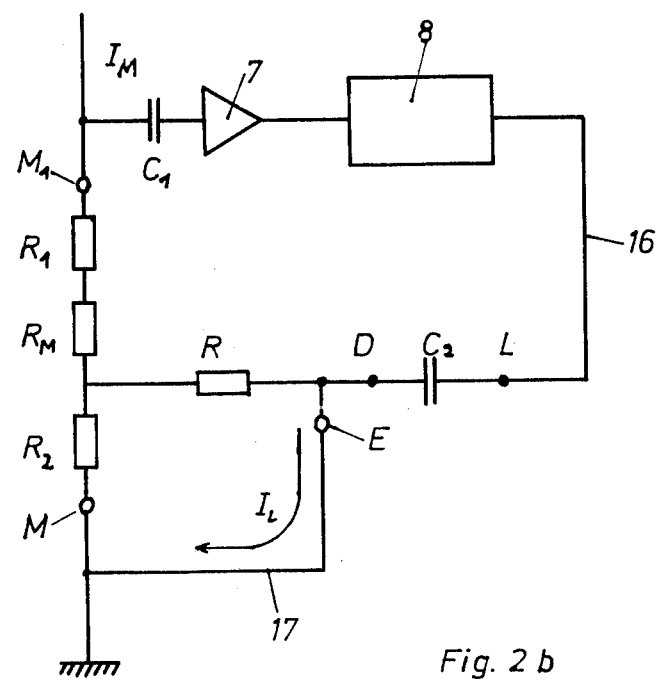
Figure 3:
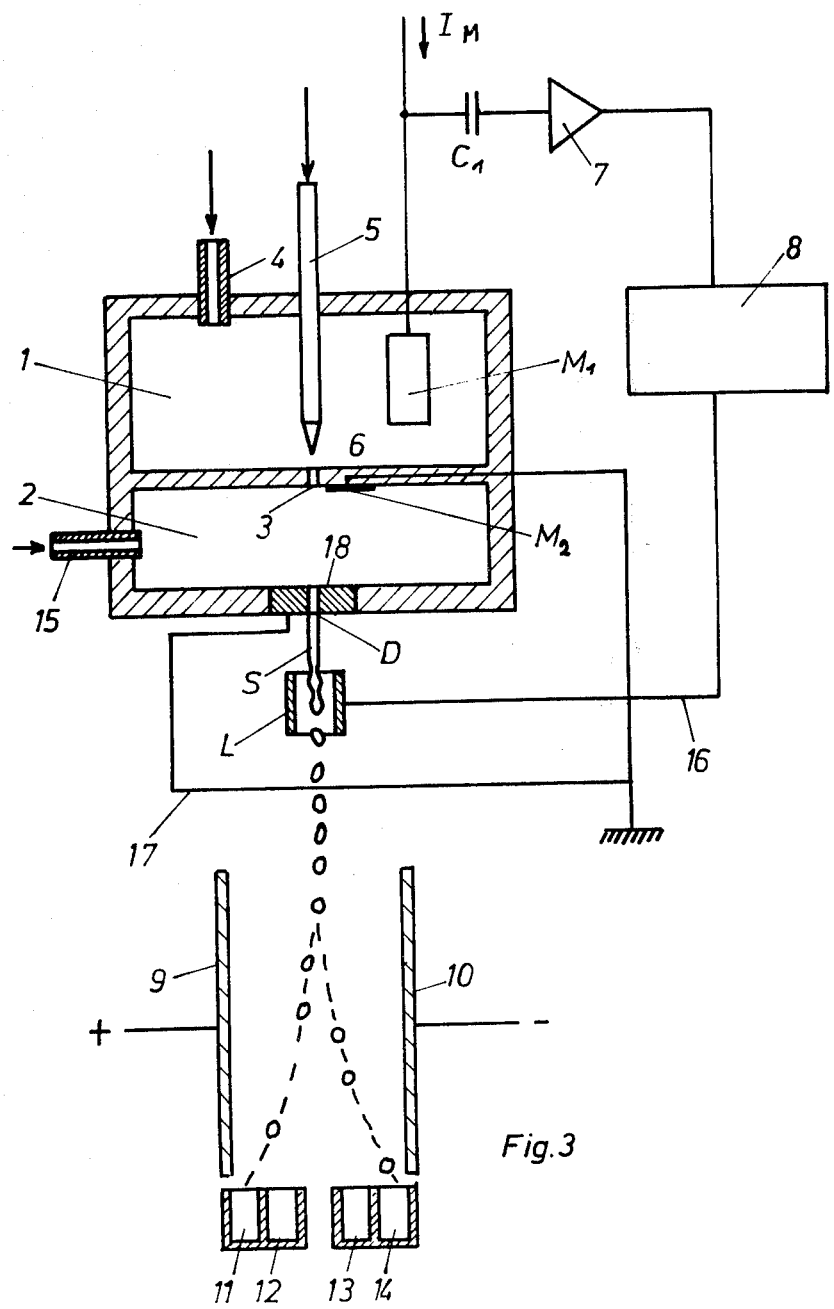
FIG. 3 is a schematic diagram of a second exemplary embodiment of the apparatus according to the invention.

Based on the foregoing analysis of the cause of the disturbances in the known apparatus, the invention provides an exemplary embodiment illustrated in FIG. 2a in which there is provided in the second chamber 2 and in the immediate vicinity of the nozzle D a secondary electrode E of relatively large surface area. At the same time, the main electrode $M_2$ is moved as close as possible to the measuring orifice 3. The electrode E is grounded as is the electrode $M_2$, i.e. the electrodes E and $M_2$ are at the same electric potential. The electric connection between the electrodes E and $M_2$ is made outside of the chamber 2 through the line 17. The presence of electrode E in the immediate vicinity of the nozzle D short-circuits the current path between the nozzle D and the electrode $M_2$ as previously formed by the resistor $R_3$ and thus prevents any coupling of the charging pulse into the measuring current circuit. The previously described disturbing pulses and voltages are thereby completely eliminated. The charging current for the charging electrode L now flows back via the line 17 and the measuring circuit as between electrodes $M_1$ and $M_2$ is uncoupled from the charging current circuit which now extends from the charging electrode L to nozzle D and hence directly to the electrode E. The equivalent circuit diagram for the first exemplary embodiment of the invention is given in FIG. 2b. The most favorable location of electrode E is as close as possible to the nozzle D. In a second exemplary embodiment of the invention illustrated in FIG. 3, the electrode E is formed by a metal ring 18 having a central bore which forms the nozzle D. In other respects, the second embodiment of FIG. 3 is identical to that of FIG. 2a. Electrode E is shown to be grounded in both exemplary embodiments, as is the electrode $M_2$. These two electrodes are shown to be connected through a line 17, the resistance of which should be as low as possible, i.e. it should be made from an especially good electrical conductor so that no or only very negligible voltage drops will be generated along this line. In general terms, the electrode E located in the vicinity of the nozzle D should be kept at the same electrical potential as the electrode $M_2$ and the connection between these two electrodes should take place through a line whose resistance is small in comparison to the resistance of the electrolyte between the two electrodes. In the first exemplary embodiment of FIG. 2a, the electrode $M_2$ is shown to lie to the right of an axis A passing through the orifice 3, whereas electrode E is shown to be to the left of axis A. This disposition insures that the electrodes are as near as possible to the measuring orifice 3 and the nozzle D, respectively, yet are separated by as large a distance as possible, thereby maximizing the resistance $R_3$ of the equivalent circuit shown in FIG. 2b and thus providing the most effective short circuit by means of the electrode E.

The foregoing relates to preferred exemplary embodiments of the invention, it being understood that other embodiments and variants thereof are possible within the spirit and scope of the invention.

What is claimed is:

1. An apparatus for separating and sorting particles which includes:

a housing defining first and second chambers which communicate through an orifice, said chambers containing an electrolytic fluid which is caused to pass from said first chamber to said second chamber;

means disposed in said first chamber for introducing into said electrolytic fluid particles for sorting and analysis;

a first electrode, disposed in said first chamber;

a second electrode, disposed in said second chamber;

means for applying an electric potential across said first and second electrodes to thereby induce a current to flow in said electrolytic fluid;

an analyzer for analyzing said current and for detecting changes in said current related to the passage of particles through said orifice;

nozzle means disposed in a wall of said second chamber, with a passage for permitting efflux of said electrolyte therefrom;

charging means for imparting an electric charge to droplets of said electrolyte exiting from said nozzle;

deflection means, for deflecting and sorting said particles according to the charge on said droplets and wherein the improvement comprises:

a third electrode, disposed in said second chamber in the immediate vicinity of said nozzle means, said third electrode being kept at the same electrical potential as said second electrode for short-circuiting the current path between said nozzle means and said second electrode to thereby eliminate disturbing pulses in the measuring circuit between said first and second electrodes.

2. An apparatus as defined by claim 1, wherein said second and third electrodes are connected to the electrical ground of said apparatus.

3. An apparatus as defined by claim 1 wherein said second and third electrodes are connected by a conductor whose electrical resistance is small compared with the effective resistance of said electrolytic fluid between said second and third electrodes.

4. An apparatus as defined by claim 1 wherein said third electrode has a relatively large effective surface.

5. An apparatus as defined by claim 1 wherein said third electrode is disposed in a wall of said second chamber and has a penetrating bore which constitutes said nozzle means permitting the passage of electrolytic fluid therethrough.

6. An apparatus as defined by claim 1 wherein the passage in said nozzle means defines an axis of said apparatus and wherein said second electrode is disposed on one side of said axis whereas said third electrode is disposed on the other side of said axis and wherein said second and third electrodes are disposed on opposite walls of said second chamber, where opposite is defined as being respectively upstream and downstream in said electrolyte.

7. An apparatus as defined by claim 1, wherein said second electrode is disposed immediately adjacent to said orifice.

* * * * *